United States Patent [19]

Slocum

[11] Patent Number: 5,578,038

[45] Date of Patent: Nov. 26, 1996

[54] JIG FOR USE IN OSTEOTOMIES

[76] Inventor: D. Barclay Slocum, 241 Spy Glass Dr., Eugene, Oreg. 97401

[21] Appl. No.: 254,478

[22] Filed: Jun. 6, 1994

Related U.S. Application Data

[63] Continuation of Ser. No. 900,726, Jun. 18, 1992, abandoned.

[51] Int. Cl.$^6$ .................................................. A61F 5/00
[52] U.S. Cl. .................................................. 606/87; 606/86
[58] Field of Search ........................... 606/54, 55, 57–59, 606/79, 82, 84–89

[56] References Cited

U.S. PATENT DOCUMENTS

| | | | |
|---|---|---|---|
| 2,251,209 | 7/1941 | Stader | 606/59 |
| 2,333,033 | 10/1943 | Mraz | 606/57 |
| 2,346,346 | 4/1944 | Anderson | 606/56 |
| 2,391,537 | 12/1945 | Anderson | 606/54 |
| 2,393,694 | 1/1946 | Kirschner | 606/59 X |
| 2,393,831 | 1/1946 | Stader | 606/59 X |
| 2,406,987 | 9/1946 | Anderson | 606/56 |
| 4,135,505 | 1/1979 | Day | 606/57 X |
| 4,488,542 | 12/1984 | Helland | 606/54 X |
| 4,509,511 | 4/1985 | Neufeld | 606/87 X |
| 4,565,191 | 1/1986 | Slocum | 606/87 |
| 4,696,293 | 9/1987 | Ciullo | 606/57 |
| 4,714,076 | 12/1987 | Comte et al. | 606/57 |
| 4,730,608 | 3/1988 | Schlein | 606/57 |
| 4,750,481 | 6/1988 | Reese | 606/87 |
| 4,848,368 | 7/1989 | Kronner | 606/57 |
| 4,922,896 | 5/1990 | Agee et al. | 606/57 X |
| 4,952,214 | 8/1990 | Comparetto | 606/87 |
| 4,978,347 | 12/1990 | Ilizarov | 606/57 X |
| 5,019,077 | 5/1991 | DeBastiani et al. | 606/59 X |
| 5,078,719 | 1/1992 | Schreiber | 606/87 |
| 5,122,140 | 6/1992 | Asche et al. | 606/57 X |
| 5,147,364 | 9/1992 | Comparetto | 606/87 X |
| 5,171,244 | 12/1992 | Caspari et al. | 606/87 X |

FOREIGN PATENT DOCUMENTS

| | | | |
|---|---|---|---|
| 3614305 | 11/1987 | Germany | 606/57 |
| 167008 | 12/1964 | U.S.S.R. | 606/57 |
| 1473762 | 4/1989 | U.S.S.R. | 606/57 |
| 2038638 | 7/1980 | United Kingdom | 606/57 |

*Primary Examiner*—Robert A. Hafer
*Assistant Examiner*—Brian E. Hanlon
*Attorney, Agent, or Firm*—Kolisch Hartwell Dickinson McCormack & Heuser

[57] ABSTRACT

A jig for use in connection with a tibial osteotomy procedure. The jig is for locating a curvilinear-cut axis prior to making a desired curvilinear cut through the tibia so that such axis is approximately normal to a plane substantially parallel to the sagittal plane. The jig includes positioner structure lying in a jig plane for positioning adjacent a desired tibial region, and aligner structure for adjusting the jig so that the jig plane is substantially parallel to a plane parallel to the sagittal plane. The positioner structure also includes locator structure that is usable, with the adjusted jig, to locate the curvilinear-cut axis. In a preferred embodiment, the positioner structure includes first and second elongate members that are pivotably interconnected with respect to each other. The first and second members are also provided with marking structure for marking the located curvilinear-cut axis and with respective first and second pins for linking the jig to the corresponding tibial bone sections. The linking pins allow the jig to be used, after making such cut, to hold neutrally the two tibial bone sections relative to one another while the proximal section is correctively rotated with respect to the distal section.

17 Claims, 2 Drawing Sheets

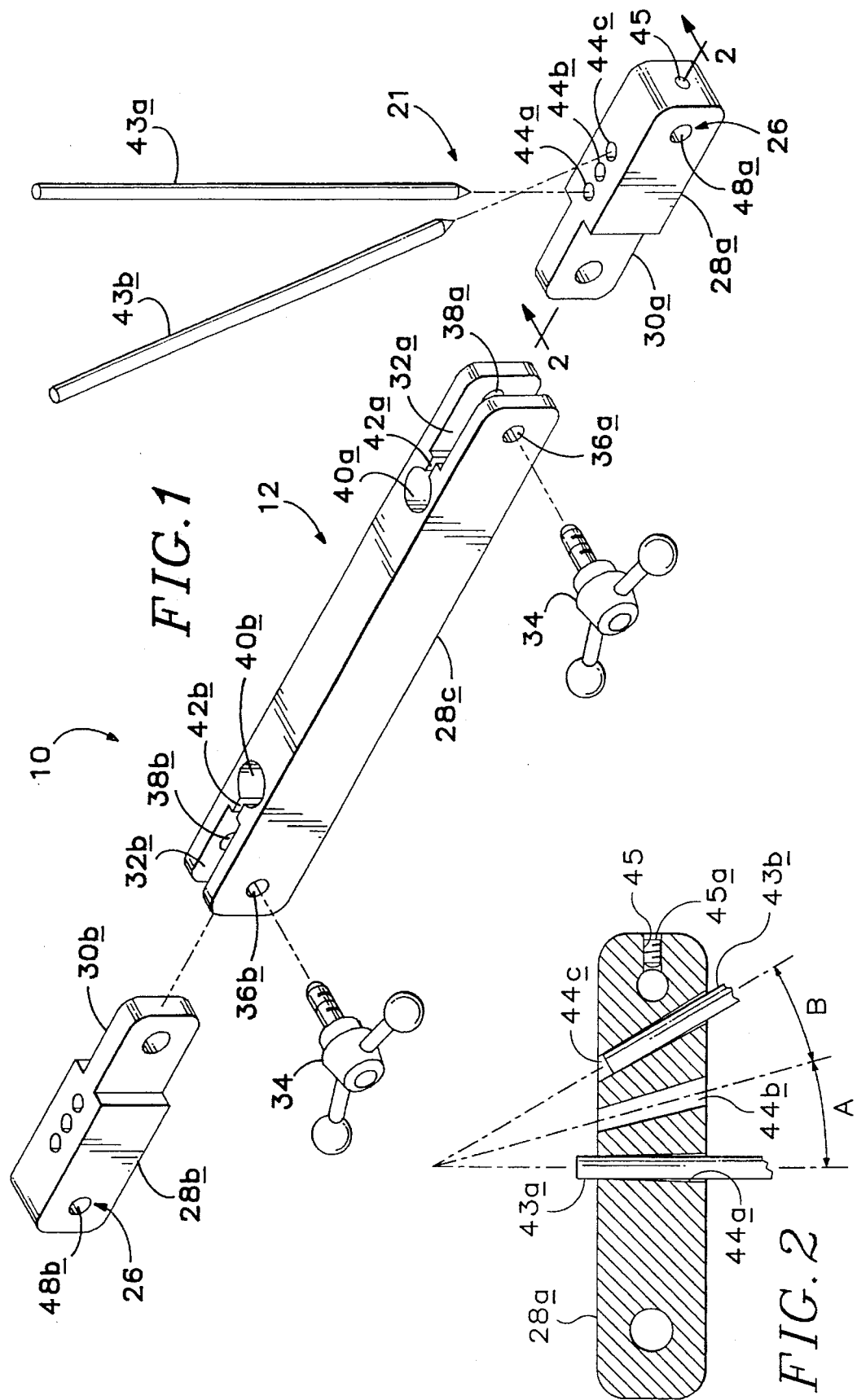

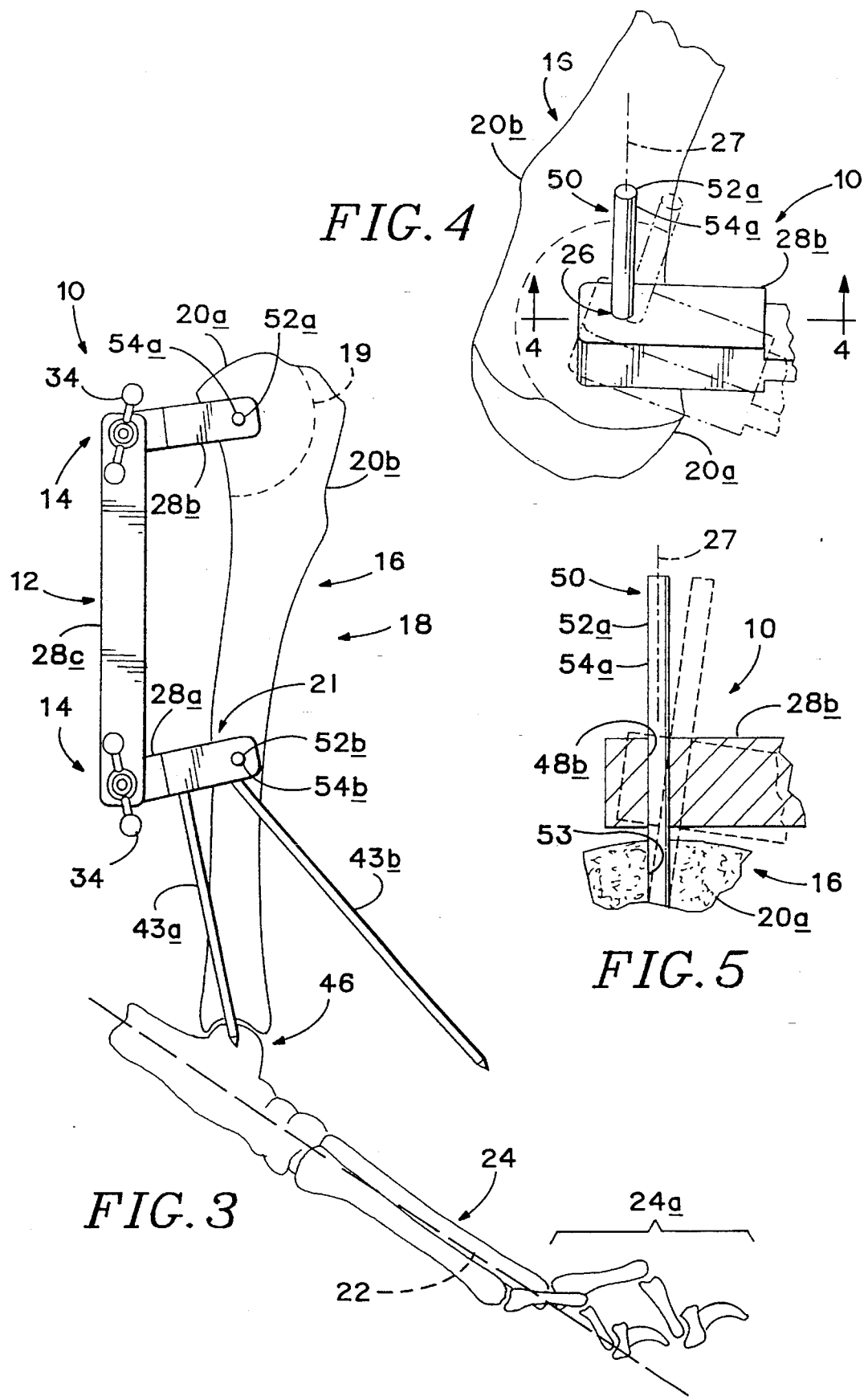

JIG FOR USE IN OSTEOTOMIES

This is a continuation of application Ser. No. 07/900,726 filed Jun. 18, 1992, now abandoned.

BACKGROUND AND SUMMARY OF THE INVENTION

The invention relates generally to devices for locating a curvilinear-cut axis about which a veterinarian makes a curvilinear cut producing a proximal and a distal bone sections in connection with an osteotomy procedure. The invention also relates generally to a post-cut step in such procedure that involves correctively rotating about such axis the proximal bone section with respect to the distal bone section. More particularly, the invention concerns a jig for locating such curvilinear-cut axis, and for holding neutrally such two tibial bone sections relative to one another during such corrective rotating.

The invention will be disclosed in the context of performing a tibial osteotomy on a canine but it should be understood that the invention is usable in tibial osteotomy procedures performed on other animals, including human beings. It should also be understood that the invention is also usable for any osteotomy procedure in which a curvilinear cut is made in a bone producing two bone sections, one of which is then correctively rotated relative to the other. Examples of such osteotomy procedures are those that are performed to correct varus or valgus conditions in animals, i.e. animals that are bowlegged or knock-kneed.

By way of background, a proximal tibial osteotomy for leveling a canine's tibial plateau involves a multi-step, cut-and-rotate approach. First, the practitioner, or veterinarian, produces in the proximal tibia a curvilinear through cut that separates it from the metaphysis. Next the veterinarian rotates the metaphysis relative to the proximal tibia a predetermined amount that effectively levels the tibial plateau. Finally, the veterinarian fixes the metaphysis relative to the proximal tibia by suitable means. Such an osteotomy is described in detail in my U.S. Pat. No. 4,677,973 entitled "Proximal, Tibial Osteotomy for Leveling A Tibial Plateau", which issued Jul. 7, 1987, the disclosure of which is incorporated herein by reference.

To begin the above multi-step approach it is necessary for the veterinarian to locate properly the curvilinear-cut axis. If the proper axis is not located then the curvilinear cut will likewise be improper, producing an improper, undesired twist in the canine's leg after the osteotomy is completed. Such curvilinear-cut axis is shown in my U.S. Pat. No. 4,955,888 entitled "Biradial Saw", which issued Sep. 11, 1990, the disclosure of which is also incorporated herein by reference. The biradial saw disclosed in that patent may be used in connection with the above-identified step of producing a curvilinear through cut that separates the metaphysis from the proximal tibia.

Focusing for a moment on the step of locating the curvilinear-cut axis, the environment of the tibial osteotomy makes it difficult to identify a proper axis because the tibia is partially covered by ligaments and other soft tissue.

Ideally, a proper curvilinear-cut axis is approximately normal to a plane that is parallel to the sagittal plane. Because the position and condition of the canine tibia is necessarily partially obstructed during the osteotomy procedure, the veterinarian has a difficult time locating such curvilinear-cut axis. Difficulty in locating the curvilinear-cut axis is also experienced because the canine is positioned during the procedure in such a way that it is difficult to identify a plane parallel to the sagittal plane.

Switching focus to the corrective-rotation step, it is important to prevent certain undesired movement to occur relative to the proximal tibial bone section and the distal (metaphyseal) tibial bone section. Of course rotation about the curvilinear-cut axis is desired, but certain other known translational and rotational movements between the two sections are undesired.

It is therefore desirable to hold neutrally the proximal and distal bone sections during corrective rotation. By holding the sections neutrally applicant means that the sections are held to allow for corrective rotation freely about the curvilinear-cut axis without also compressing the sections together. For a further description of undesired compression between the two sections, see the disclosure in my copending application, Ser. No. 07/822,402, entitled "Tibial Osteotomy Fixation Plate", which disclosure is also incorporated herein by reference. In that application I discuss, among other things, the desirability of selectively compressing/distracting the two bone sections with my novel fixation plate. To ensure that selective compression/distracting is possible when the sections are fixed together, it is important that premature compression/distraction does not take place during corrective rotation. If the sections are held neutrally adjacent each other during corrective rotation no such premature compression/distraction takes place.

Accordingly, it is a principle object of the present invention to provide a jig for locating the curvilinear-cut axis about which a curvilinear through cut is made to separate the metaphysis from the proximal tibia during a procedure referred to as a tibial plateau-leveling osteotomy (TPLO) procedure.

Another object is to provide such a jig that accommodates holding neutrally the proximal and distal tibial bone sections after such curvilinear cut has been made and during corrective rotation of the proximal bone section relative to the distal bone section.

A still further object of the present invention is to provide a jig that will prevent premature compression/distraction of the proximal and distal bone sections while at the same time being usable to hold the bone sections after such curvilinear cut has been made and during corrective rotation of the proximal bone section relative to the distal bone section.

Yet another object of the invention is to provide such jig that is usable in osteotomy procedures for animals of disparate sizes.

Another object is to provide a jig for use with a fixation plate in such TPLO procedure, the jig facilitating accurate and secure relative rotation and fixation of the bone sections, as well as accurate and secure placement and alignment of the fixation plate.

SUMMARY OF THE INVENTION

Applicant has achieved the above objects by providing a jig for locating the curvilinear-cut axis in connection with a tibial osteotomy procedure performed on an animal. Briefly, the procedure in which the jig of the present invention is used involves the use of cutting apparatus to make a curvilinear cut about the curvilinear-cut axis through a tibia of a leg that includes a hock joint, tarsus, and metatarsus, where the cut will produce proximal and distal tibial bone sections, and the proximal section will be correctively rotated relative to the distal section.

The jig includes positioner structure lying in a jig plane for positioning adjacent a desired portion of the tibia, and aligner structure for adjusting the jig so that the jig plane is substantially parallel to a plane that is parallel to the sagittal plane. The positioner structure includes locator structure that is usable, after the jig is adjusted, to locate the curvilinear-cut axis. The aligner structure may be used to adjust the jig plane to include a plane which includes the long axis of the metatarsus.

The invention may also embody a jig including a first elongate member and a second elongate member connected to the first member. Both members lie in a jig plane and are positionable adjacent a desired portion of the tibia. Pointer structure extends from the first member for adjusting the jig so that the jig plane is substantially parallel to a plane that includes the long axis of the metatarsus. The second member includes locator/guide structure that is usable, with the adjusted jig, to locate the curvilinear-cut axis prior to cutting the tibia. The locator/guide structure is also usable to guide a drill for forming a recess in the tibia along such axis, which recess receives marking structure to mark such axis and thereby assist the veterinarian in making the curvilinear cut about such axis.

In the preferred embodiment of the invention the first and second members are made pivotable relative to one another, and the first member is provided with first means for linking the jig to the distal tibial bone section and the second member is provided with second means for linking the jig to the proximal tibial bone section so that, after such cut is made with such cutting apparatus, the jig is usable to hold neutrally the two tibial bone sections relative to one another while the proximal section is correctively rotated with respect to the distal section.

These and additional objects and advantages of the present invention will be more readily understood after a consideration of the drawings and the detailed description of the preferred embodiment.

BRIEF DESCRIPTION OF THE DRAWINGS

FIG. 1 shows an exploded perspective view of the jig of the present invention.

FIG. 2 is a sectional view through line 2—2 of FIG. 1.

FIG. 3 is a side view of the jig of the present invention lying in a jig plane and positioned adjacent the proximal tibial region on the medial side of a canine's left leg and viewed from a vantage point located medially therefrom.

FIG. 4 is a fragmentary perspective view of the jig shown in FIG. 3, on a slightly larger scale and having been rotated approximately 180°, showing a section of the jig in an unadjusted position (dashed lines) and adjusted position (solid lines).

FIG. 5 is a fragmentary sectional view through line 4—4 of FIG. 4 again showing a section of the jig in an unadjusted position (dashed lines) and adjusted position (solid lines).

DETAILED DESCRIPTION OF THE PREFERRED EMBODIMENT

Referring to FIG. 1, the preferred embodiment of the jig of the present invention is shown at 10 including positioner structure 12. It should be understood that jig 10 is usable in connection with performing proximal tibial osteotomies on animals, including human beings, and in particular on canines.

Referring to FIG. 3, positioner structure 12 lies in jig plane 14 (represented by the plane in which the drawing sheet lies), and is positioned adjacent the proximal tibial region 16 on the medial side of a canine's left leg 18. The osteotomy will be performed by making a curvilinear cut, shown by dashed arcuate line 19, which will separate tibial region 16 into proximal tibial section 20a and distal tibial section 20b.

Referring to FIGS. 1 and 3, aligner structure 21 also forms part of jig 10 and is usable, as will be described, to adjust the jig so that jig plane 14 is substantially parallel to a plane that includes the long axis 22 of a metatarsus 24 of a canine (remainder of canine body undepicted). Metatarsus 24 terminates in a paw 24a which includes toes, or digits, one of which is shown in FIG. 3. The significance of jig 10 to the toes of paw 24a will be described.

Referring to FIG. 1, positioner structure 12 includes locator structure 26 that is usable, as will be described, to locate curvilinear-cut axis 27 (FIGS. 4 and 5) after jig 10 is adjusted. Referring to FIGS. 1 and 3, positioner structure 12 includes first, second and third elongate members 28a,28b, 28c. First and second members 28a,28b are pivotably connected to third member 28c by placing their respective tab sections 30a,30b into slots 32a,32b formed in opposite ends of third member 28c. The first and second members are held in position relative to the third member by using dogs 34 which are slidably received in holes 36a,b of third member 28c and threadably received in threaded holes 38a,b of third member 28c.

Still referring to FIG. 1, compression fastening of the first and second members to the third member with dogs 34 is accomplished by providing a pair of cylindrical bores 40a,b which are formed in third member 28c and communicate with corresponding slots 30a,b via channels 42a,b. Alternatively, compression fastening can be accomplished by extending slots 32a,32b inwardly approximately as far as bores 40a,b.

Maintaining focus on positioner structure 12 shown in FIGS. 1 and 3, it should be understood that the same may take various forms other than the depicted substantially C-shaped configuration with three members. The C-shape is preferred because it accommodates offsetting substantially the jig during the TPLO procedure to allow the veterinarian substantial access to the working area of tibial region 16.

As for variations on the form of positioner structure 12, the pivotable connection between second member 28b and third member 28c could be omitted and those two members could be formed as one substantially straight member so that positioner structure 12 would have a substantially triangular shape. For reasons that will be apparent after reading this entire description, positioner structure 12 must have at least one pivotable connection. Briefly, and referring to FIG. 3, the reason for this requirement is to allow the jig to be used, after the curvilinear cut is made, to hold neutrally the two tibial bone sections 20a,b relative to one another while proximal section 20a is correctively rotated with respect to distal section 20b.

Switching focus to aligner structure 21, FIGS. 1 and 3 show that it preferably takes the form of two rods 43a, 43b. The rods are extendable in corresponding openings 44a–c. Referring to FIG. 3, rod 43a is structured and positionable in aligner structure 21 to extend toward the distal region of metatarsus 24 while rod 43b is structured and positionable to extend toward the proximal region of the tarsus, i.e. the bones between metatarsus 24 and tibia 20. Still referring to FIG. 3, rod 43a is preferably structured with an extent that allows it to be positioned over hock joint (specifically the medial malleolus) 46 and rod 43b preferably has an extent which allows it to be directed toward the metatarsus, and preferably toward the area between the second and third rays of paw 24a.

Referring to FIG. 2, aligner structure 21 is preferably structured with plural tapered openings 44a–c for selective use with rods 42a,b to accommodate a range of canine (or other animal) leg sizes. For example, FIGS. 2 and 3 show a relatively wide angle (approximately 30°–angle A (15°)+ angle B (15°)) being defined by inserting the rods in openings 44a and 44c to accommodate a canine with a relatively large leg 18 and metatarsus 24. Referring to FIG. 2, an alternative and smaller angle A (15°) could be defined by the rods for a smaller canine by placing rod 43b through opening 44b with rod 43a being placed through opening 44a.

Still referring to FIG. 2, openings 44a–c each have corresponding top and bottom portions, with the openings being tapered upwardly so that the diameters of the top portions are smaller than the diameters of rods 43a,b, thereby preventing the rods from extending through the top portions as shown by rod 43b in FIG. 2 and rods 43a,b in FIG. 3. Focusing attention to rod 43b in FIG. 2, it is clear that the rod is cylindrical and therefore can only extend a certain distance upwardly into hole 44c because of the upward taper. By suitably tapering the corresponding end of rod 43a and/or rod 43b, as shown for rod 43a in FIG. 2, it has been found that the rod can be modified to extend slightly through the top, tapered end of hole 44c (in contrast to rod 43b being prevented from so extending if it were not tapered as shown in FIG. 2). With such slight upward extension through the top tapered portion of the holes, the rod ends can be tapped with a hammer to remove them from the holes when desired.

FIG. 2 also shows that first member 28a is formed with a threaded bore 45 for receiving a set screw 45a which is usable to fix the vertical position relative to the tibia of to-be-described means for linking the jig to corresponding tibial bone sections.

Referring to FIGS. 3–5, and focusing again on positioner structure 12, first and second members 28a,b are formed with locator structure 26 which includes corresponding holes 48a,b (FIG. 5) with long axes that are substantially normal to jig plane 14. Holes 48a,b are structured to receive marking structure 50 for locating curvilinear-cut axis 27. Such marking structure preferably includes pins 52a,b which are fittable in recesses drilled into tibial section 16 (one such recess 53 shown in FIG. 5) using conventional drilling apparatus (undepicted). The marking structure could take any form that is usable to mark the curvilinear-cut axis after it is located, as will soon be described, using jig 10.

Referring to FIG. 3 but continuing to focus on holes 48a,b, both holes should be usable to receive pins 52a,b for locating the curvilinear-cut axis so that jig 10 can also be used on the medial side of a tibial region (undepicted) like region 16 but on the right leg (undepicted) of the canine whose left leg is depicted in FIG. 3. To use jig 10 on such medial side of the right leg, the jig would be rotated 180° from its position in FIG. 3 so that first member 28a is where second member 28b is and vice versa.

Another feature of holes 48a,b is that they are deep enough so that the surfaces of first and second members 28a,b that define them will guide a drill bit (undepicted) that is placed through a desired one of them (in FIG. 5 the desired hole is hole 48b) for movement along the curvilinear-cut axis to drill recess 53 for inserting pin 52a. Once the drill bit extends through hole 48a to form recess 53, the same procedure is followed to form a recess (undepicted) for pin 52b.

Still referring to FIGS. 3–5, first and second means 54a,b for linking the jig to corresponding tibial bone sections are also provided. Preferably, first and second linking means are formed as pins 52a,b, which, in the preferred embodiment, are also usable as marking structure 50.

OPERATION

Referring to FIGS. 3–5, jig 10 of the present invention is usable to locate curvilinear-cut axis 27 by first positioning it adjacent tibial region 16. Next, aligner structure 21, which may also be thought of as pointer structure, is adjusted so that it lies in a plane that includes long axis 22 of metatarsus 24. By so adjusting aligner structure 21, jig 10 is adjusted so that jig plane 14 is substantially parallel to a plane that is parallel to the sagittal plane (i.e. a plane that includes long axis 22 of metatarsus 24).

With the jig in its adjusted position (see solid-line depiction of jig 10 in FIGS. 4 and 5), the curvilinear-cut axis is located and can be marked by drilling recess 53 (FIG. 5) in tibial section 20a and placing pin 52a in it. Pin 52a, which now represents a properly located curvilinear-cut axis, may be used with curvilinear cutting apparatus such as my above-identified biradial saw to make a curvilinear through cut along dashed arcuate line 19 (FIG. 3).

Referring to FIG. 3, and for reasons soon to be described, a recess is also drilled in tibial section 20b and pin 52b is placed in it so that jig 10 may be linked to tibial region 16 after the curvilinear through cut is made in it. After both recesses are drilled, jig 10 may be removed, i.e. unlinked, from the tibial region to allow optimal access to the working area during the curvilinear cutting procedure. Of course pin 52a would remain in place to mark curvilinear-cut axis 27 during cutting about it along arcuate line 19. Also, jig 10 may be left in a linked position and its vertical position relative to tibia 20 may be fixed by turning set screws (undepicted) in suitably formed threaded bores of members 28a,b such as threaded bore 45 shown in FIG. 2.

If the jig is unlinked from the tibia before making the cut, it may be relinked to the bone sections after the cut is made and before tibial bone section 20a is correctively rotated according to the TPLO procedure. By relinking the jig to the bone sections, the jig is used to hold them neutrally relative to one another and to allow for desired movement of the bone sections. Such desired movement of the bone sections includes (1) corrective rotation about the curvilinear-cut axis, (2) translational movement up and down with respect to leg 18, and (3) translational movement forward and backward with respect to leg 18. Jig 10 will however prevent other types of undesired relative motion between tibial sections 20a,b, thereby assisting the veterinarian in performing the corrective rotation step of the TPLO procedure.

While the present invention has been shown and described with reference to the foregoing preferred embodiment, it will be apparent to those skilled in the art that other changes in form and detail may be made therein without departing from the spirit and scope of the invention as defined in the appended claims.

I claim:

1. An osteotomy jig comprising:
   a positioner structure through which parallel first and second holes are formed, with each hole defining a longitudinal axis;

a first rod extending outwardly from the positioner structure adjacent the first hole, extending outwardly from the positioner structure in a jig plane which is normal to the longitudinal axis of the first hole; and a second rod extending outwardly from the positioner structure in a predetermined fixed angular relationship relative to the first rod adjacent the first hole, diverging from the first rod and extending outwardly from the positioner structure in the jig plane;

a third hole formed in and extending into the positioner structure and lying in the jig plane, wherein the first rod is inserted into the third hole;

a fourth hole formed in and extending into the positioner structure and lying in the jig plane at the acute angle relative to the third hole, wherein the second rod is inserted into the fourth hole; and a fifth hole formed in and extending into the positioner structure and lying in the jig plane at approximately a 30 and 15 degree angle relative to the third and fourth holes, respectively;

wherein the first and second rods define an acute angle of approximately 15 degrees and thereby define the jig plane normal to the longitudinal axis of the first hole.

2. The jig of claim 1 wherein:

the jig is for use on an animal with a hock joint, tibia, tarsus and metatarsus;

the first rod is for extending toward a distal region of the metatarsus;

the second rod is for extending toward a proximal region of the tarsus, thereby aligning the jig plane with respect to a long axis of the metatarsus and placing the first hole substantially perpendicular to a sagittal plane of the animal; and the first hole is for placement over a desired portion of the tibia to serve as a guide to locate a curvalinear cut axis.

3. The jig of claim 2 wherein the first rod has an extent that allows it to be positioned over the hock joint and the second rod has an extent that allows it to be directed toward the metatarsus.

4. The jig of claim 2 further comprising a first link for linking the jig to the desired portion of the tibia.

5. The jig of claim 4, wherein the second hole is for placement over a distal portion of the tibia relative to the desired portion.

6. The jig of claim 5, further comprising a second link for linking the jig to the distal portion of the tibia so that, after a curvalinear cut is made in the tibia with a cutting apparatus, the jig is usable to hold neutrally the two portions of the tibia relative to one another while the desired portion of the tibia is rotated correctively with respect to the distal portion.

7. The jig of claim 6 wherein the first and second links each includes a pin.

8. The jig of claim 1 wherein:

the positioner structure comprises a first member and a second member that are pivotable relative to one another;

the first member comprises a first link for linking the jig to a desired tibial bone section; and the second member comprises a second link for linking the jig to a distal tibial bone section so that, after the desired section is cut from the distal section, the jig is usable to hold neutrally the two tibial bone sections relative to one another while the desired tibial bone section is correctively rotated with respect to the distal tibial bone section.

9. The jig of claim 8 wherein the first and second links each include a pin.

10. The jig of claim 1 wherein the positioner structure comprises:

a first member through which the first hole extends; and a second member operatively connected to the first member, and from which the first and second rods extend.

11. The jig of claim 10 wherein the positioner structure further comprises a third member operatively connecting the first member to the second member.

12. The jig of claim 1 wherein the positioner structure comprises:

a first, a second, and a third member, with the first and second members pivotally connected to the third member, wherein the first, second and third members are coplanar and define a positioner plane that is parallel to the jig plane.

13. The jig of claim 1 further comprising:

a first pin removably inserted into the first hole and having an end that extends outwardly from the positioner structure; and a second pin removably inserted into the second hole and having an end that extends outwardly from the positioner structure.

14. The jig of claim 13 further comprising:

a first set screw communicating with the first hole for fixing the first pin relative to the positioner structure; and a second set screw communicating with the second hole for fixing the second pin relative to the positioner structure.

15. The jig of claim 1 wherein the third and fourth holes are tapered so that the first and second rods are held in the third and fourth holes, respectively, by an interference fit.

16. The jig of claim 15 wherein one end of each of the first and second rods is tapered to conform approximately to the third and fourth holes, respectively.

17. An osteotomy jig comprising:

a positioner structure through which parallel first and second holes are formed, with each hole defining a longitudinal axis;

a first rod extending outwardly from the positioner structure adjacent the first hole, extending outwardly from the positioner structure in a jig plane which is normal to the longitudinal axis of the first hole; and a second rod extending outwardly from the positioner structure in a predetermined fixed angular relationship relative to the first rod adjacent the first hole, diverging from the first rod and extending outwardly from the positioner structure in the jig plane;

a third hole formed in and extending into the positioner structure and lying in the jig plane, wherein the first rod is inserted into the third hole;

a fourth hole formed in and extending into the positioner structure and lying in the jig plane at the acute angle relative to the third hole; and a fifth hole formed in and extending into the positioner structure and lying in the jig plane at approximately a 30 and 15 degree angle relative to the third and fourth holes, respectively, wherein the second rod is inserted into the fifth hole;

wherein the first and second rods define an acute angle of approximately 30 degrees and thereby define the jig plane normal to the longitudinal axis of the first hole.

* * * * *